US012605177B2

(12) United States Patent
McNulty et al.

(10) Patent No.: US 12,605,177 B2
(45) Date of Patent: Apr. 21, 2026

(54) MANUAL DEBRIDING PAD

(71) Applicant: Solventum Intellectual Properties Company, Maplewood, MN (US)

(72) Inventors: Amy K. McNulty, Stillwater, MN (US); Amy S. Determan, Mahtomedi, MN (US); Sarah L. Isakson, St. Anthony, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 546 days.

(21) Appl. No.: 17/799,946

(22) PCT Filed: Apr. 26, 2021

(86) PCT No.: PCT/IB2021/053414
§ 371 (c)(1),
(2) Date: Aug. 16, 2022

(87) PCT Pub. No.: WO2021/224714
PCT Pub. Date: Nov. 11, 2021

(65) Prior Publication Data
US 2023/0067731 A1     Mar. 2, 2023

Related U.S. Application Data

(60) Provisional application No. 63/020,823, filed on May 6, 2020.

(51) Int. Cl.
*D03D 15/283*     (2021.01)
*A61B 17/32*     (2006.01)
(Continued)

(52) U.S. Cl.
CPC .......... *A61B 17/32* (2013.01); *A61F 13/0008* (2013.01); *A61F 13/01021* (2024.01); *D03D 1/00* (2013.01); *D03D 15/283* (2021.01); *D03D 15/292* (2021.01); *D03D 27/00* (2013.01); *D04B 1/04* (2013.01); *D04B 1/22* (2013.01);
(Continued)

(58) Field of Classification Search
None
See application file for complete search history.

(56) References Cited

U.S. PATENT DOCUMENTS 3,561,441 A      2/1971  Lombardi
4,306,555 A  *  12/1981  Ritter ...................... A61F 13/38
19/145.3
(Continued)

FOREIGN PATENT DOCUMENTS

EP       2777662 A1     9/2014
EP       3539517 A1     9/2019

OTHER PUBLICATIONS

International Search Report for PCT International Application No. PCT/IB2021/053414, mailed on Jul. 29, 2021, 7 pages.

*Primary Examiner* — Jenna L Johnson

(57) ABSTRACT
An example debriding pad includes a support layer, a first region, and a second region. The first region includes a first material defining a plurality of first loop piles arranged on the support material. The second region includes a second material defining a plurality of second loop piles arranged on the support material. The second material is stiffer than the first material to provide more aggressive debridement of a wound.

20 Claims, 7 Drawing Sheets

(51) Int. Cl.

| | |
|---|---|
| *A61F 13/00* | (2024.01) |
| *A61F 13/01* | (2024.01) |
| *D03D 1/00* | (2006.01) |
| *D03D 15/292* | (2021.01) |
| *D03D 27/00* | (2006.01) |
| *D04B 1/04* | (2006.01) |
| *D04B 1/22* | (2006.01) |
| *D04B 21/04* | (2006.01) |
| *D04B 21/16* | (2006.01) |
| *D04B 21/20* | (2006.01) |

(52) U.S. Cl.
CPC ........... *D04B 21/04* (2013.01); *D04B 21/165* (2013.01); *D04B 21/20* (2013.01); *A61B 2017/320004* (2013.01); *D10B 2321/021* (2013.01); *D10B 2321/022* (2013.01); *D10B 2331/04* (2013.01); *D10B 2509/00* (2013.01)

(56) References Cited

U.S. PATENT DOCUMENTS

| | | | | |
|---|---|---|---|---|
| 5,902,661 A * | 5/1999 | Oster | .................... | A63B 57/60 |
| | | | | 428/85 |
| 7,273,648 B2 * | 9/2007 | Morin | ................... | D03D 27/00 |
| | | | | 428/92 |
| 9,713,553 B2 * | 7/2017 | Engl | ....................... | A61F 13/36 |
| 2021/0007764 A1 * | 1/2021 | Wilhelms | ............... | A61B 17/54 |

* cited by examiner

FORMING, ON SUPPORT LAYER, FIRST LOOP PILES FROM FIRST MATERIAL TO DEFINE FIRST REGION — 202

FORMING, ON SUPPORT MATERIAL, SECOND LOOP PILES FROM SECOND MATERIAL TO DEFINE SECOND REGION — 204

FOLDING SUPPORT LAYER TO DEFINE A POCKET — 206

SECURING AT LEAST ONE FIRST FREE EDGE OF SUPPORT LAYER TO AT LEAST ONE SECOND FREE EDGE OF SUPPORT LAYER TO FORM DEBRIDING PAD — 208

MANUAL DEBRIDING PAD

CROSS REFERENCE TO RELATED APPLICATIONS

This application is a national stage filing under 35 U.S.C. 371 of PCT/IB2021/053414, filed Apr. 26, 2021, which claims the benefit of U.S. Provisional Application No. 63/020,823, filed May 6, 2020, the disclosure of which is incorporated by reference in its entirety herein.

TECHNICAL FIELD

The present application is related to articles, systems, and techniques for wound debriding.

BACKGROUND

Wound debriding may include the removal of slough, necrotic tissue, microbial load (e.g., bacteria and biofilms), from wounds, such as chronic and/or hard to heal wounds, in order to promote healing. Debridement may be performed by several methods, including physically with abrasives or surgical incisive tools (e.g., sharp debridement), chemically with debriding enzymes or lotions, and mechanically with negative pressure, water jets, and wipes. Each procedure has limitations. For example, surgical debridement may include a lengthy, complicated procedure performed at a medical facility by skilled medical personnel. Chemical debridement may be limited by slow action and cost. Mechanical debridement may require equipment and skilled personnel and may be limited by cost.

SUMMARY

The disclosure is related to articles, systems, and techniques for wound debriding The described articles, systems, and techniques include a debriding pad that includes a first relatively soft region including a plurality of first loop piles of a first material and a second relatively aggressive region including a plurality of second loop piles of a second material.

In some examples, the disclosure is directed to a debriding pad defining a first region and a second region. The debriding pad includes a support layer, a first region, and a second region. The first region includes a first material defining a plurality of first loop piles arranged on the support material. The second region includes a second material defining a plurality of second loop piles arranged on the support material. The second material is stiffer than the first material.

In some examples, the disclosure is directed to a method of forming a debriding pad. The method includes forming, on a support layer, a plurality of first loop piles that include a first material to define a first region. The method also includes forming, on the support layer, a plurality of second loop piles that include a second material to define a second region. The method also includes folding the support layer to define a pocket. The method also includes securing at least one first free edge of the support layer to at least one second free edge of the support layer to form a debriding pad.

In some examples, the disclosure is directed to a method of debriding a wound. The method includes wetting at least a portion of a debriding pad. The debriding pad includes a support layer, a first region, and a second region. The first region includes a first material defining a plurality of first loop piles arranged on the support material. The second region includes a second material defining a plurality of second loop piles arranged on the support material. The second material is stiffer than the first material. The method also includes applying the debriding pad to a wound with a selected a pressure. The method also includes moving the debriding pad to debride at least a portion of the wound.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

Like symbols in the drawings indicate like elements.

DETAILED DESCRIPTION

The present disclosure describes articles, systems, and techniques that include debriding pads defining a first region including a relatively softer loop pile configuration and a second region including a relatively stiffer loop file configuration. The described articles, systems, and techniques provide for simple, inexpensive, and effective debridement that can be performed by caregivers or patients in-home or at clinics. Additionally, or alternatively, the described articles, systems, and techniques provide at least a relatively softer region, which may improve patient comfort during debridement of relatively sensitive wounds, and a relatively aggressive region, which may improve removal of more adherent slough and/or reduce time required for adequate debridement.

Figure 1A:
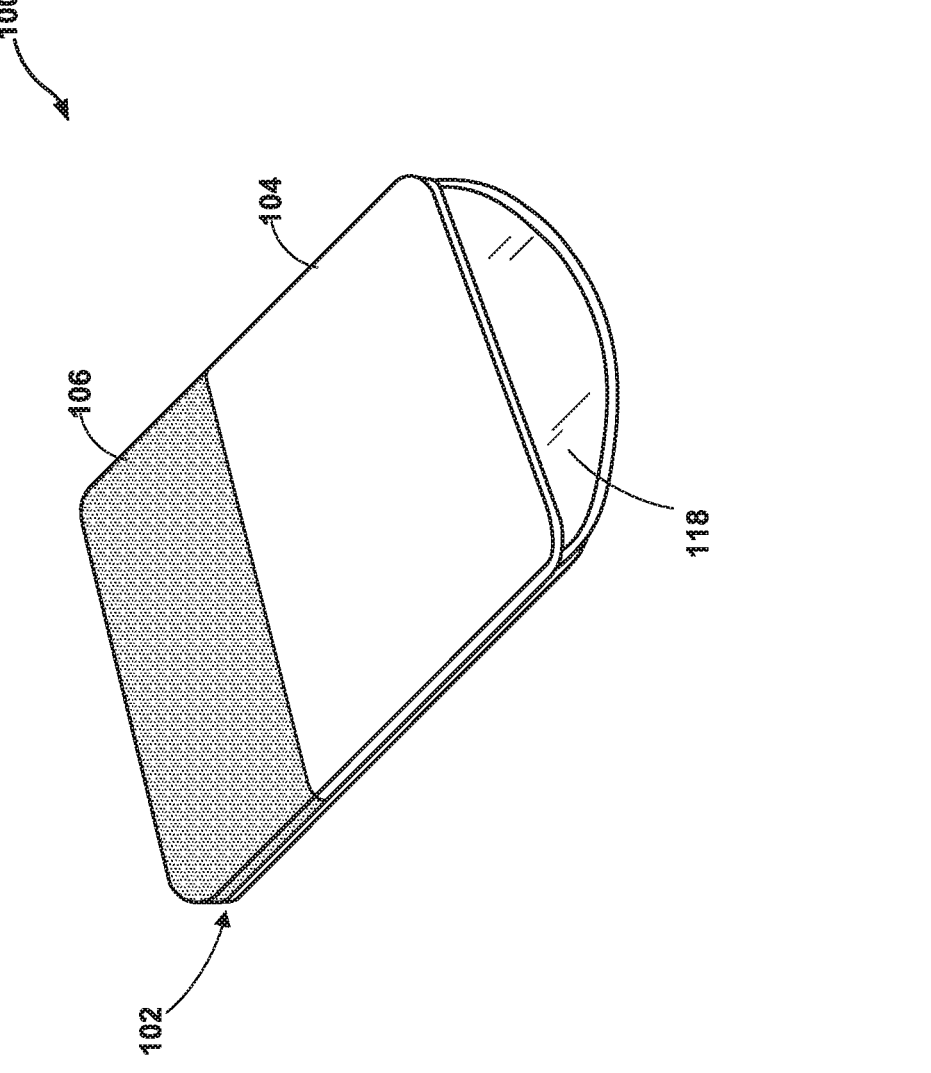
FIG. 1A is a conceptual perspective view of an example debriding pad that includes a relatively soft region and a relatively aggressive region.
Figure 1B:
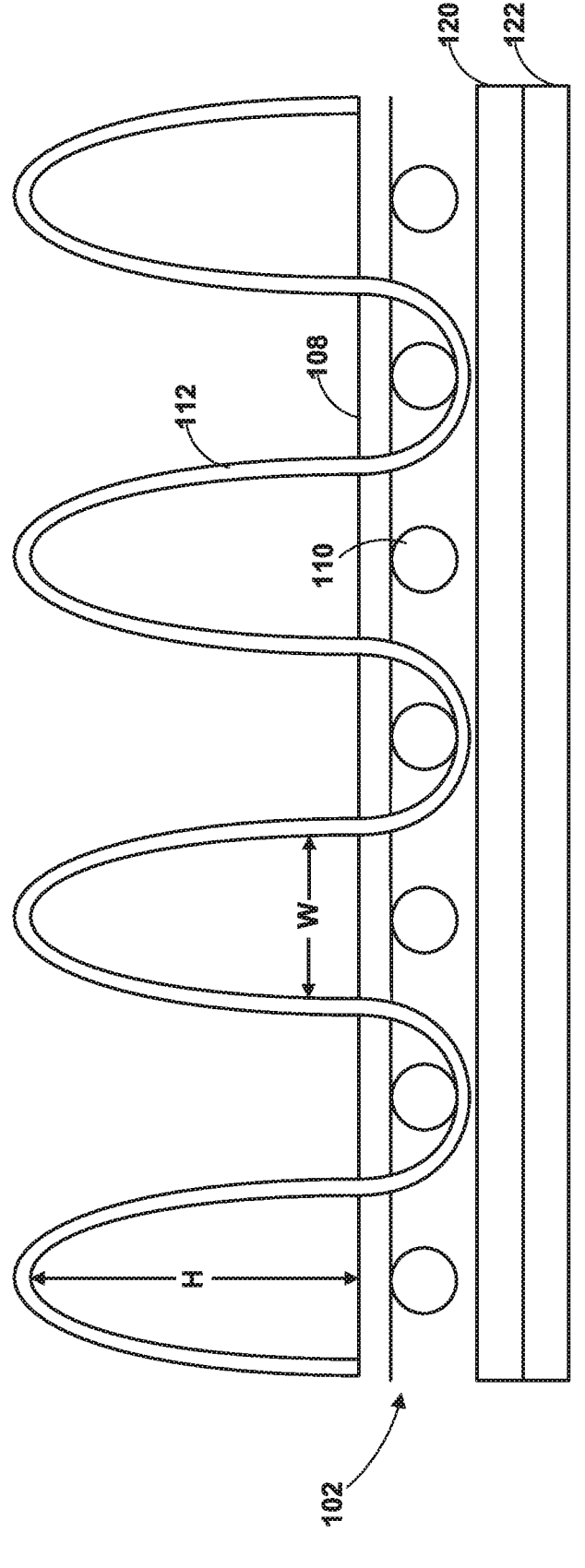
FIG. 1B is a conceptual diagram illustrating a cross-sectional view of the relatively soft region of the example debriding pad.
Figure 1C:
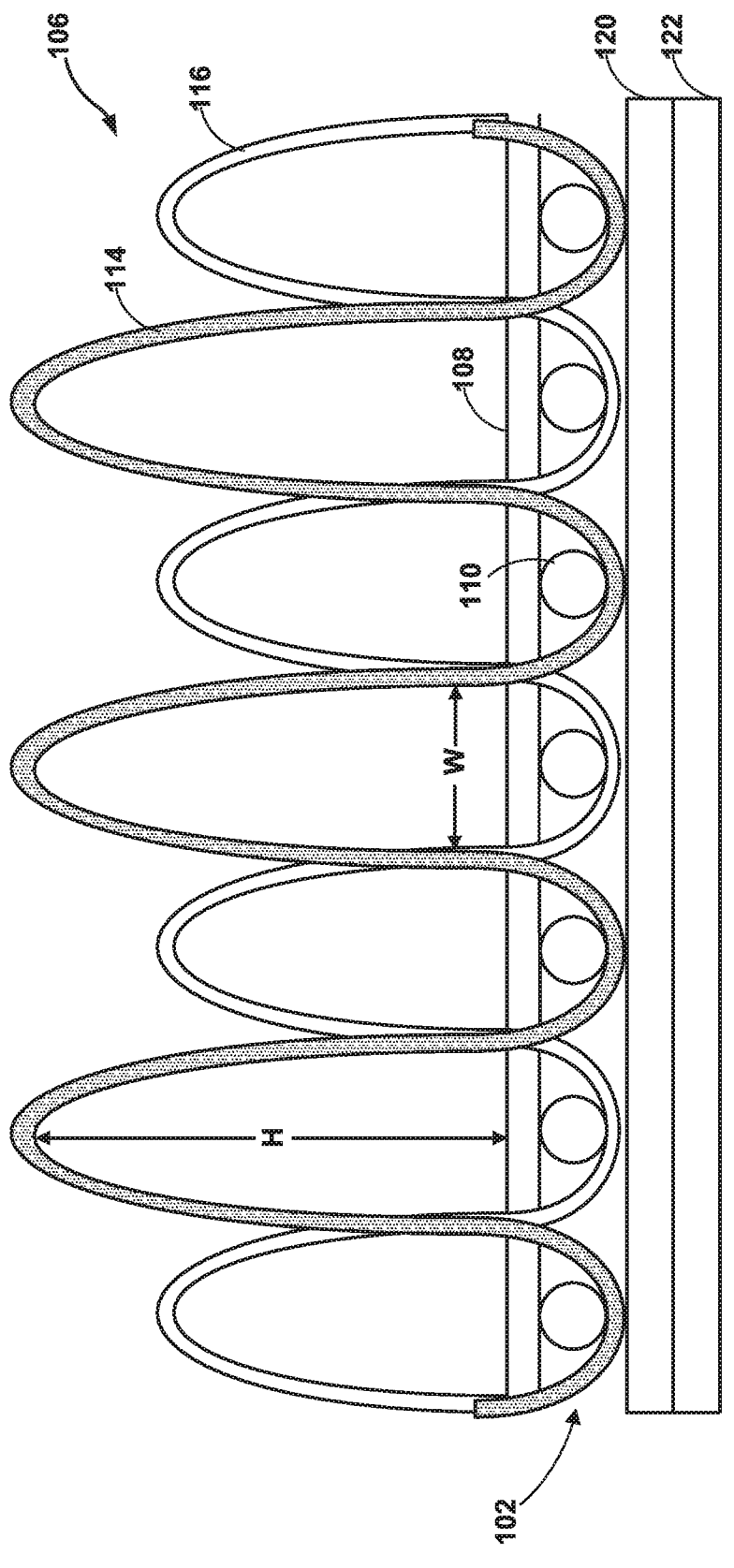
FIG. 1C is a conceptual diagram illustrating a cross-sectional view of the relatively aggressive region of the example debriding pad.

FIG. 1A is a conceptual perspective view of an example debriding pad 100 that includes a relatively soft region and a relatively aggressive region. Debriding pad 100 includes a support layer 102, a first region 104 (e.g., the relatively soft region), and a second region 106 (e.g., the relatively aggressive region). FIG. 1B is a conceptual diagram illustrating a cross-sectional view of the relatively soft first region 104. FIG. 1C is a conceptual diagram illustrating a cross-sectional view of the relatively aggressive second region 106. Although first region 104 and second region 106 are illustrated in FIG. 1A as disposed on the same side of debriding pad 100, in other examples, first region 104 and second region 106 may be disposed on opposing sides of debriding pad 100, or debriding pad 100 may include a plurality of first regions 104 and/or a plurality of second regions 106. In some examples, the position and/or the number of first region 104 and second region 106 may be selected to improve debridement of a wound by, for example, enabling improved control of a pressure applied via debriding pad 100 to a wound and/or a movement of debriding pad 100 relative to a wound during a debridement procedure.

Support layer 102 is configured to provide structure to which yarn or threads may be fixed by, e.g., knitting, knotting, weaving, adhering, or the like. In some examples, support layer 102 may include woven or nonwoven fibers, threads, or yarns defining a scrim. The scrim may include a coarse-woven fabric and/or gauze. In some examples, as illustrated in FIG. 1B, support layer 102 may include one or more warp yarns 108 having a linear density within a range from about 200 denier to about 1000 denier. For example, support layer 102 may include first warp yarns having a linear density of about 500 denier and second warp yarns having a linear density of about 840 denier. In some examples, support layer 102 may include one or more weft yarns 110 having a linear density within a range from about 1000 denier to about 3000 denier. For example, support layer 102 may include weft yarns 110 having a linear density of about 2000.

Support layer 102 may include any suitable material or combination of materials. Example materials may include one or more of olefins, polyesters, natural polyesters, rayon, cotton, combinations thereof, or the like. In some examples, the material of support layer 102 may be selected to maintain structural integrity during a sterilization procedure using, for example, steam, ethylene oxide, dry heat, hydrogen peroxide vapor, gamma radiation, e-beam, or one or more other sterilants.

As illustrated in FIG. 1B, first region 104 includes a first material defining a plurality of first loop piles 112 (first loop piles 112) arranged on support material 102. First region 104 may be configured to loosen wound tissue to be debrided, retain debrided material in the first plurality of loop piles, and/or provide more gentle debridement compared to, for example, second region 106. First loop piles 112 may be arranged on support material 102 by knitting, knotting, weaving, adhering, or otherwise fixing the first material with at least one of warp threads 108 or weft threads 110 of support material 102. For example, first loop piles 112 may be knitted into a scrim of support material 102.

First loop piles 112 may include any suitable construction, shape, and/or density. In some examples, the selected to construction, shape, and/or density of first loop piles 112 may be selected to gently loosen and retain debrided wound tissue. For example, each loop pile of first loop piles 112 may include any suitable number of yarns. In some examples, each loop pile of first loop piles 112 may include two or more yarns, such as four yarns. The yarns may be braided or unbraided. Multiple yarns in each loop may, in some examples, improve an ability of first loop piles 112 to loosen and/or retain debrided wound tissue. In some examples, the yarns may define a chenille yarn including, for example, a pile between two core yarns that are twisted together.

First loop piles 112 may be any suitable height. For example, an average loop height H relative to support layer 102 of first loop piles 112 may be within a range from about 5 millimeters (mm) to about 10 mm, such as within a range from about 7 mm to about 8 mm. In some examples, the loop height H of each first loop pile of first loop piles 112 may be substantially similar, e.g., within common tolerances of textile manufacturing techniques. In some examples, the loop height H of each first loop pile of loop piles 112 may regularly or irregularly vary. For example, a first portion of the first loop piles 112 may include a first average height and a second portion of first loop piles 112 may include a second average height different than the first average height. The selected height of first loop piles 112 may, in some examples, improve an ability of first loop piles 112 to loosen and/or retain debrided wound tissue. For example, a relatively shorter loop pile may offer improved debridement, e.g., loosening of tissue to be debrided, compared to a relatively longer loop pile. A relatively longer loop pile may have improved debrided tissue retention, e.g., able to retain a larger volume of debrided tissue, compared to a relatively shorter loop pile.

First loop piles 112 may be any suitable width. For example, an average loop width W first loop piles 112, e.g., a maximum distance between opposing portions of a loop pile measured parallel to support layer 102, may be within a range from about 0.5 mm to about 10 mm, such as within a range from about 0.09 mm to about 2 mm. In some examples, the loop width W of each first loop pile of first loop piles 112 may be substantially similar, e.g., within common tolerances of textile manufacturing techniques. In some examples, the loop width W of each loop pile of first loop piles 112 may regularly or irregularly vary. For example, a first portion of the first loop piles 112 may include a first average width and a second portion of first loop piles 112 may include a first average width. The selected width of first loop piles 112 may, in some examples, improve an ability of first loop piles 112 to loosen and/or retain debrided wound tissue. For example, a relatively thinner loop pile may have improved debridement, e.g., loosening of tissue to be debrided, compared to a relatively wider loop pile. A relatively wider loop pile may have improved debrided tissue retention, e.g., able to retain a larger volume of debrided tissue, compared to a relatively thinner loop pile.

First loop piles 112 may be arranged on support material 102 in any suitable density and/or knitting pattern. For example, a density of first loop piles 112 may be within a range from about 50 stiches per inch to about 400 stiches per inch, such as within a range from about 200 stiches per inch to about 300 stiches per inch, such as about 270 stiches per inch. Stich per inch may be equal to the product of course per inch and wales per inch. In some examples, a course per inch of first loop piles may be within a range from about 5 course per inch to about 30 course per inch, such as about within a range from about 10 course per inch to about 20 course per inch, such as about 18 courses per inch. In some examples, a wales per inch of first loop piles may be within a range from about 5 wales per inch to about 30 wales per inch, such as about within a range from about 10 wales per inch to about 20 wales per inch, such as about 15 courses per inch. In some examples, a selected density of first loop piles 112 may, in some examples, improve an ability of first loop piles 112 to loosen and/or retain debrided wound tissue. For example, a first density of first loop piles 112 may have improved loosening of wound tissue and/or retain a larger volume of debrided wound tissue, compared to a second loop pile. In some examples, a density of first loop piles 112 may be selected based on experimental data, such as data obtains from experimental removal of orange pith, or other experimental data indicative of an ability to loosen and/or retain debrided wound tissue.

First loop piles 112, or the yarns defining first loop piles, may include any suitable linear mass density. In some examples, a linear mass density of the first material is within a range from about 50 denier to about 500 denier, such as between about 100 denier and 300 denier. In some examples, the first material may include 225 denier textured natural polyester.

First loop piles 112 may include any suitable material or combination of materials. Example materials may include one or more of olefins, polyesters, natural polyesters, acrylic, high density polyethylene (HDPE), polyethylene terephthalate (PET), fluorinated ethylene propylene (FEP), rayon, cotton, combinations thereof, or the like. In some examples, the material of first loop piles 112 may be selected to maintain structural integrity during a sterilization procedure using, for example, steam, ethylene oxide, dry heat, hydrogen peroxide vapor, gamma radiation, or one or more other sterilants.

Second region 106 includes a second material defining a plurality of second loop piles 114 (second loop piles 114) arranged on the support material, wherein the second material is stiffer than the first material. For example, second region 106 may be configured to more aggressively loosen debrided wound tissue, such as slough (e.g., necrotic tissue, wet necrotic tissue, dry necrotic tissue, and/or fibrotic tissue), compared to first region 104. Second loop piles 114 may be arranged on support material 102 by knitting, knotting, weaving, adhering, or otherwise fixing the first material with at least one of warp threads 108 or weft threads 110 of support material 102. For example, second loop piles 114 may be knitted into a scrim of support material 102.

Second loop piles 114 may include any suitable construction, shape, and/or density selected such that second loop piles 114 are stiffer relative to first loop piles 112. For example, second loop piles 114 may have a greater bending rigidity and/or greater flexural rigidity relative to first loop piles 112. In this way, the selected to construction, shape, and/or density of second loop piles 114 may be selected to more aggressively loosen debrided wound tissue compared to first loop piles 112. For example, second lop piles 114 may loosen more slough from a wound per pass with the same amount of pressure on debriding pad 100 compared to first loop piles 112.

Each loop pile of second loop piles 114 may include any suitable number of yarns. In some examples, each loop pile of second loop piles 114 may include one yarn. The yarns may be braided or unbraided. In some examples, a single, relatively stiff yarn may, in some examples, improve an ability of second loop piles 114 to loosen adherent slough to reduce time to debride a wound, reduce pressure require to debride a wound, and/or improve patient comfort during debridement, compared to other types of yarn.

Second loop piles 114 may be any suitable height. For example, an average loop height H2 relative to support layer 102 of second loop piles 114 may be within a range from about 1 mm to about 20 mm, such as within a range from about 2 mm to about 10 mm or within a range from about 7 mm to about 8 mm. In some examples, the loop height H2 of each first loop pile of second loop piles 114 may be substantially similar, e.g., within common tolerances of textile manufacturing techniques. In some examples, the loop height H2 of each loop pile of second loop piles 114 may regularly or irregularly vary. For example, a first portion of the second loop piles 114 may include a first average height and a second portion of second loop piles 114 may include a second average height different than the first average height. The selected height of second loop piles 114 may, in some examples, improve an ability of second loop piles 114 to loosen adherent slough. For example, a relatively shorter loop pile may have improved debridement, e.g., loosening of slough, compared to a relatively longer loop pile. A relatively longer loop pile may have improved debride retention, e.g., able to retain a larger volume of debride, compared to a relatively shorter loop pile.

Second loop piles 114 may be any suitable width. For example, an average loop width W2 second loop piles 114, e.g., a maximum distance between opposing portions of a loop pile measured parallel to support layer 102, may be within a range from about 1 mm to about 20 mm, such as within a range from about 2 mm to about 10 mm or within a range from about 7 mm to about 8 mm. In some examples, the loop width W2 of each loop pile of second loop piles 114 may be substantially similar, e.g., within common tolerances of textile manufacturing techniques. In some examples, the loop width W of each loop pile of second loop piles 114 may regularly or irregularly vary. For example, a first portion of the second loop piles 114 may include a first average width and a second portion of second loop piles 114 may include a first average width. The selected width of second loop piles 114 may, in some examples, improve an ability of second loop piles 114 to loosen slough. For example, a relatively thinner loop pile defining a more incisive tip may have improved loosening of slough compared to a relatively wider loop pile defining a blunter tip. A relatively wider loop pile may have improved debride retention, e.g., able to retain a larger volume of debride, and/or improve patient comfort during debridement compared to a relatively thinner loop pile.

Second loop piles 114 may be arranged on support material 102 in any suitable density and/or knitting pattern. For example, a density of second loop piles 114 may be within a range from about 50 stiches per inch to about 400 stiches per inch, such as within a range from about 200 stiches per inch to about 300 stiches per inch. Stich per inch may be equal to the product of course per inch and wales per inch. In some examples, a course per inch of first loop piles may be within a range from about 10 course per inch to about 30 course per inch, such as about within a range from about 15 course per inch to about 20 course per inch, or about 18 courses per inch. In some examples, a wales per inch of first loop piles may be within a range from about 10 wales per inch to about 30 wales per inch, such as about within a range from about 15 wales per inch to about 20 wales per inch, or about 15 wales per inch. In some examples, a selected density of second loop piles 114 may, in some examples, improve an ability of second loop piles 114 to loosen and/or retain debrided wound tissue. For example, a first density of second loop piles 114 may have improved loosening of debridement tissue and/or retain a larger volume of debrided tissue, compared to a second loop pile. In some examples, a density of second loop piles 114 may be selected based on experimental data, such as data obtains from experimental removal of orange pith, or other experimental data indicative of an ability to loosen and/or retain debrided wound tissue.

Second loop piles 114, or the yarns defining first loop piles, may include any suitable linear mass density. In some examples, a linear mass density of the second material is within a range from about 1000 denier to about 2000 denier, such as between about 1200 denier and 1800 denier, or about 1440 denier.

Second loop piles 114 may include any suitable material or combination of materials. Example materials may include one or more of olefins, polyesters, natural polyesters, rayon, cotton, combinations thereof, or the like. In some examples, the material of second loop piles 114 may be selected to be stiffer compared to the material of first loop piles 112. For example, the material second loop piles 114 may have a greater Young's modulus relative to the material of first loop piles 112. In some examples, the material of second loop piles 114 may be selected to maintain structural integrity during a sterilization procedure using, for example, steam, ethylene oxide, dry heat, hydrogen peroxide vapor, gamma radiation, or one or more other sterilants. In some examples, the material of second loop piles 114 may include polyester monofilament yarn.

In some examples, debriding pad 100 may be configured for manual mechanical debridement by hand or using a tool. For example, debriding pad 100 may define a pocket 118. Pocket 118 may be size to receive at least a portion of a hand of a clinician, patient, or other person performing a debridement procedure. In some examples, pocket 118 may extend into substantially an entirety of debriding pad 100 or through debriding pad 100. In some examples, pocket 118 may define one or more channels configured to receive one or more fingers of a hand of a person performing a debridement procedure. By sizing pocket 118 to fit at least a portion of a hand of a person performing a debridement procedure, debriding pad 100 may improve control of debridement pad 100 during the debridement procedure to improve control of the motion of debridement pad 100 and/or pressure applied via debridement pad 100 to a wound to at least one of enhance debridement of slough, reduce time required for debridement, or improve patient comfort during the debridement procedure.

In some examples, rather than receiving at least a portion of a hand, pocket 118 may receive a portion of a tool. For example, pocket 118 may be sized to receive a distal end of a wand or other elongate tool having a proximal handle that may be manipulated by a person performing a debridement procedure. By sizing pocket 118 to receive a distal end of a wand, debriding pad 100 may improve control of debridement pad 100 during the debridement procedure to improve control of the motion of debridement pad 100 and/or pressure applied via debridement pad 100 to a wound to at least one of enhance debridement of slough, reduce time required for debridement, or improve patient comfort during the debridement procedure. Additionally, or alternatively, the wand may enable or improve debridement of deep wounds or hard to reach wounds compared to a debridement pad that is not configured to be used with a wand.

In some examples, second region 106 may include one or more additional materials defining one or more respective pluralities of additional loop piles. For example, as illustrated in FIG. 1C, second region 106 may include a plurality of third loop piles 116 (third loop piles 116) arranged on support material 102. Second loop piles 114 and third loop piles 116 may be arranged in any suitable manner, such as, for example, a one-in one-out pattern. In some examples, third loop piles 116 may be the same as or substantially similar to first loop piles 112 described above. For example, third loop piles 116 may include the same material as first loop piles 112 and/or be arranged in any one or more configurations of first loop piles described above.

In some examples, debriding pad 100 may include additional layers and/or additional regions. For example, the additional layers and/or regions may be configured to absorb fluids, define a moisture resistant barrier, and/or provide different degrees of debridement.

In some examples, debriding pad 100 may include at least one absorbent layer 120. The at least one absorbent layer may be configured to absorb fluids, biological fluids, blood, plasma, saline, water, or other fluids used or produced during wound debridement. The at least one absorbent layer may be adjacent support layer 102, opposite first loop piles and/or second loop piles. The at least one absorbent layer may include any suitable material or combination of materials configured to absorb fluids, such as, for example, cellulose fibers, cotton, water-absorbent polymers, hydrogels, or other materials configured to absorb aqueous solutions.

In some examples, debriding pad 100 may include at least one moisture resistant layer 122. The at least one moisture resistant layer may be configured to provide a barrier to fluids, biological fluids, blood, plasma, saline, water, or other fluids used or produced during wound debridement. The at least one moisture resistant layer may be adjacent support layer 102, or adjacent the optional absorbent layer, opposite first loop piles and/or second loop piles. The at least one moisture resistant layer may include any suitable material or combination of materials resistant or impermeable to fluids, such as, for example, a polymeric film, a woven polymeric fabric, a nonwoven polymeric fabric, polyethylene, polypropylene, polyamide, polyethylene terephthalate, polystyrene, or the like.

In some examples, debriding pad 100 may include an antimicrobial. The antimicrobial may be disposed on or within any one of support layer 102, first regions 104, second region 106, other layer of debriding pad 100, or within an antimicrobial layer that is separate from other layers of debriding pad 100. The antimicrobial may include any suitable antimicrobial for use on wounds that require debridement. For example, the antimicrobial may include one or more of iodine; iodophors; N-vinyl caprolactam containing polymers; chlorhexidine salts; octenidine salts; parachlorometaxylenol (PCMX); triclosan; hexachlorophene; fatty acid monoesters of glycerin and propylene glycol such as glycerol monolaurate, glycerol monocaprylate, glycerol monocaprate, propylene glycol monolaurate, propylene glycol monocaprylate, propylene glycol monocaprate; phenols; surfactants and polymers that include a C12-C22 hydrophobe and a quaternary ammonium group; polyquaternary amines such as polyhexamethylene biguanide; quaternary silanes; hydrogen peroxide; silver and silver salts such as silver chloride, silver oxide and silver sulfadiazine; or other antimicrobials configured for use on wounds.

In some examples, debriding pad 100 may be included in a kit for debriding a wound. An example kit may include debriding pad 100, instructions, one or more solutions, one or more moisture absorbent members, personal protective equipment, one or more bandages, or other articles used in debriding procedures. The instructions may include information related to performing a debridement procedure using debriding pad 100. The information may be presented in one or more of text, images, video, or audio. The kit also may include one or more solutions for wetting debriding pad 100, rinsing the wound, or both. The one or more solutions may include, for example, water, saline, a wound cleansing solution, a disinfectant, or other solution used in debridement procedures. The kit also may include one or more moisture absorbent articles for drying the wound, e.g., after rinsing debride from the wound, dressing the wound, or both. The one or more moisture absorbent articles may include, for example, gauze, towels, pads, or other articles suitable for absorbing excess moisture on or around the wound. The kit also may include personal protective equipment that may be used by a person performing a debridement procedure to reduce transmission of pathogens, bodily fluids, or both. The personal protective equipment may include, for example, one or more of safety glass or goggles, a face shield, gloves, a gown, a drape, tape, or a mask. The kit also may include one or more bandages for dressing the wound after debridement. The one or more bandages may include any suitable bandages, such as sterile pads, gauze, wraps, tape, self-adhesive bandages, or the like.

Figure 2:
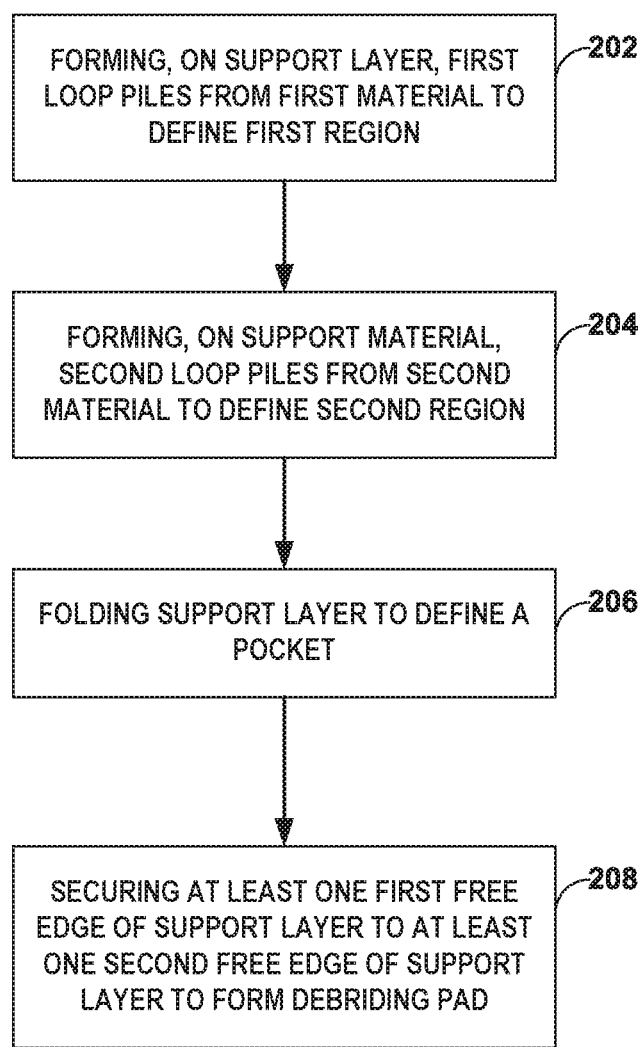
FIG. 2 is a flow diagram illustrating an example technique of forming a debriding pad.

FIG. 2 is a flow diagram illustrating an example technique of forming a debriding pad. Although the technique illustrated in FIG. 2 will be described in reference to debriding pad 100 described in reference to FIGS. 1A-1C, the technique may be used to form other debriding pads, and other techniques may be used to form debriding pad 100.

The technique illustrated in FIG. 2 includes forming, on support layer 102, first loop piles 112 from a first material to define first region 104 (202). In some examples, forming first loop piles 112 may include knitting the first material to support layer 102. For example, forming first loop piles 112 may include knitting the first material into support layer using a flat crochet, multi-bar electronic knitting machine to form first pool piles 112. In one examples, the electronic knitting machine may include a 15 gauge needle bed, although any suitable needle bed may be used based on a selected material of support layer 102, a selected material of first loop piles 112, and/or a selected construction, shape, and density of first loop piles 112. In some examples, forming first loop piles 112 may include other textile manufacturing techniques to knot, weave, adhere, or otherwise fix or secure a first material to support layer 102 to form first loop piles 112.

In some examples, forming first loop piles 112 may include forming, e.g., by knitting or the like, on support layer 102, a continuous length of debriding fabric. The continuous length of debriding fabric may include two or more debriding pads. The technique also may include cutting portions of the continuous length of debriding fabric to define at least one debriding pad 100.

The technique illustrated in FIG. 2 also includes forming, on support material 102, second loop piles 114 from a second material to define second region 106 (204). Forming second loop piles 114 may include the same or substantially similar techniques as discussed above for forming first loop piles 112. As discussed above, the second material may stiffer than the first material or otherwise provide more aggressive debridement of a wound, for example, to remove adherent slough.

In some examples, the technique may include, before or after forming second loop piles 114, forming, on support layer 102, third loop piles 116 from the first material to define or within second region 106. Forming third loop piles 116 may include the same or substantially similar techniques as discussed above for forming first loop piles 112. In some examples, second loop piles 114 may be formed at the same time as, or sequentially with, third loop piles 116.

The technique illustrated in FIG. 2 also includes folding support layer 102 to define a pocket 118 (206). Folding support layer 102 may include manual or automated folding. In examples in which forming first loop piles 112 and/or second loop piles 114 includes forming a continuous length of debriding fabric, folding support layer 102 may include folding the debriding fabric to define a cavity comprising a plurality of pockets 118 of respective debriding pads. In some examples, after folding support layer 118, first region 104 may be disposed on a first side of pocket 118, e.g., a first face of debriding pad 100, and second region 106 may be disposed on a second side of pocket 118 opposite the first side of pocket 118, e.g., a second face of debriding pad 100 opposite the first side of debriding pad 100.

The technique illustrated in FIG. 2 also includes securing at least one first free edge of support layer 102 to at least one second free edge of support layer 102 to form debriding pad 100 (208). The free edges of support layer 102 may include portions of support layer 102 adjacent to perimeter boundaries of support layer 102, first region 104, and/or second region 106. In some examples, securing the at least one free edge of the support layer to the at least one second free edge of the support layer may include impulse welding, ultrasonic welding, thermal welding, stitching, or otherwise fastening at least a portion of first free edge to at least a portion of second free edge. In some examples, securing may be performed to reduce or prevent formation of features, such as sharp or hard features, that may cause discomfort to a patient when debriding a wound. In some examples, the technique also may include trimming excess material, e.g., excess regions of support layer 102, first region 104, and/or second region 106, from debriding pad 100.

Figure 3:
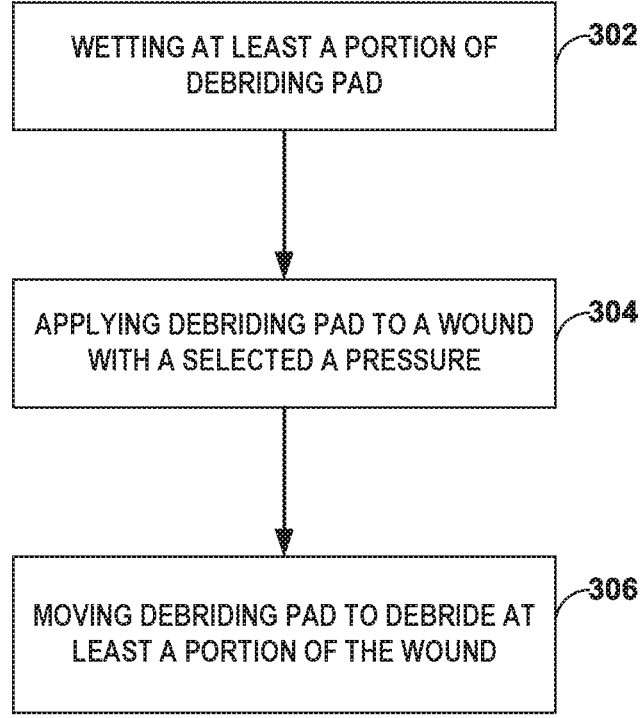
FIG. 3 is a flow diagram illustrating an example technique of using a debriding pad.

FIG. 3 is a flow diagram illustrating an example technique of using a debriding pad. Although the technique illustrated in FIG. 3 will be described in reference to debriding pad 100 described above in reference to FIGS. 1A-1C, the technique may be used with other debriding pads, and debriding pad 100 may be used with other techniques.

The technique illustrated in FIG. 3 includes wetting at least a portion of debriding pad 100 (302). For example, wetting debriding pad 100 may include submerging or soaking debriding pad 100 in a fluid or applying a fluid to at least a portion of debriding pad 100. The fluid may include any suitable fluid for using in a debriding procedure, such as, for example, water, saline, a chemical debridement solution, or a biological debridement solution. In some examples, after wetting debriding pad 100, the technique may include wringing excess fluid out of debriding pad 100.

The technique illustrated in FIG. 3 also includes applying debriding pad 100 to a wound with a selected a pressure (304). The selected pressure may be based at least in part on at least one of a sensitivity of the wound, an amount of slough, a type of wound, or a location of wound. For example, the selected pressure may be within a range from about 0.25 Newtons (N) about 20 N. In some examples, the selected pressure may be less than 0.25 N or greater than 20 N.

The technique illustrated in FIG. 3 also includes moving debriding pad 100 to debride at least a portion of the wound (306). In some examples, moving debriding pad 100 may include moving debriding pad 100 in a regular motion, such as a circular motion about the wound or a lateral motion across the wound. In some examples, the technique may include moving debriding pad 100 for a selected period of time to debride the wound. For example, the selected period of time may be within a range from about 30 seconds to about 5 minutes, such as within a range from about 1 minute to about 2 minutes.

EXAMPLES

Figure 4A:
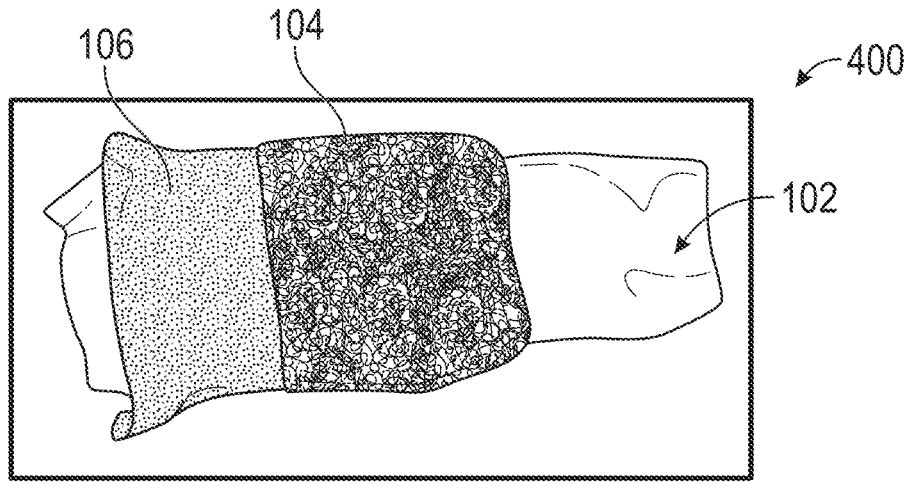
FIGS. 4A-4C are photographs illustrating an example debriding pad prior and after folding and securing for define the debriding pad.
Figure 4B:
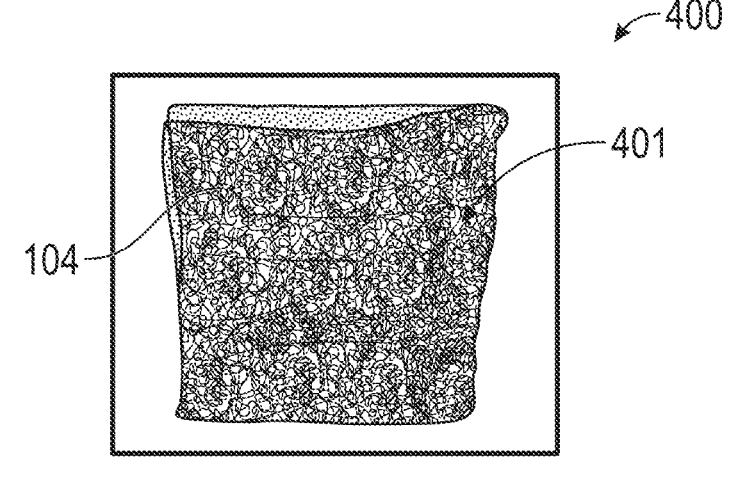
Figure 4C:
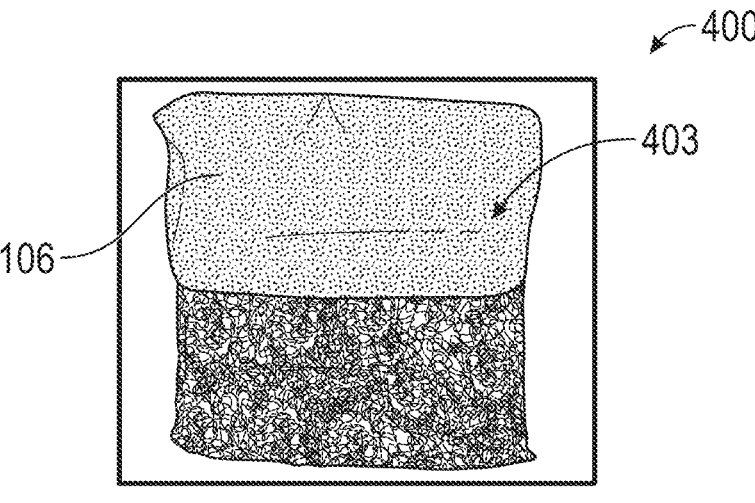

FIGS. 4A-4C are photographs illustrating an example debriding pad 400. FIG. 4A illustrates debriding pad 400 after knitting, on support layer 402, a first material to form first loop piles in relatively soft region 404, a second material to form second loop piles in relatively aggressive region 406, and the first material to form third loop piles in relatively aggressive region 406. FIGS. 4B and 4C illustrate debriding pad 400 after folding and ultrasonic welding. FIG. 4B illustrates relatively soft region 404 disposed primarily on a first side 401 of debriding pad 400. FIG. 4C illustrates relatively aggressive region 406 disposed primarily on a second side 403, opposite first side 401, of debriding pad 100.

Figures 5A, 5B, 5C:
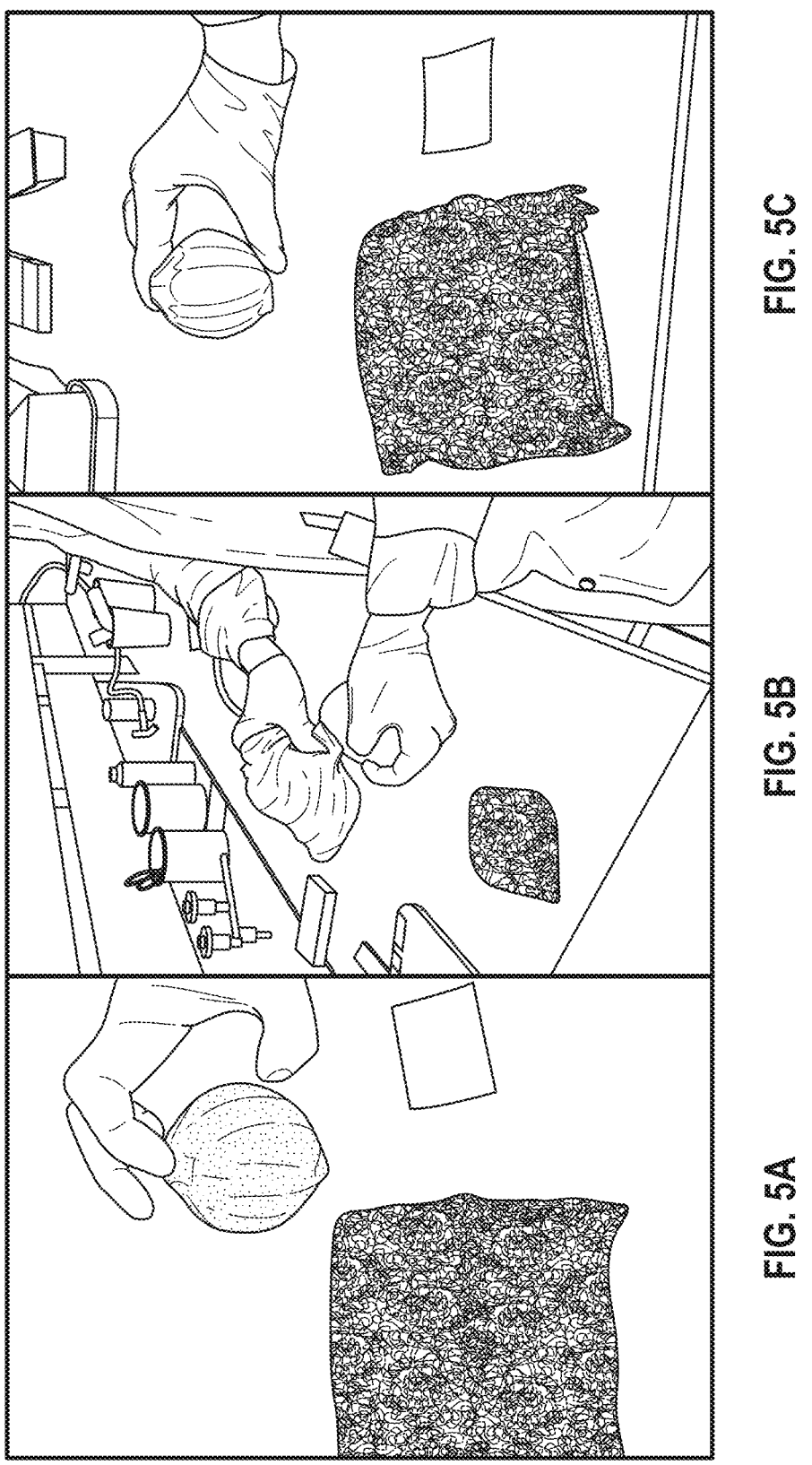
FIGS. 5A-5C are photographs illustrating an example use of a debriding pad to remove orange pith.

FIGS. 5A-5C are photographs illustrating an example use of a debriding pad to remove orange pith. The orange pith removal test was performed using example debriding pads described herein. The orange pith removal test includes the following steps. The peel of navel oranges purchased from a local grocery store were removed. Using a marker, orange thread combinations and higher loop density led to better pith removal and less bottoming out compared to greater loop height or lower loop density.

| Sample | Loops/ Sq. In. | Loop Height (mm) | Thread Diameter & Type | Pith Removal | Trauma | Shedding | Bottoming out |
|---|---|---|---|---|---|---|---|
| A | 1581 | 0.23 | .0075" HDPE and 600d PET | 3 | 1 | 1 | 1 |
| B | 1222 | 0.24 | .0075" HDPE and 450d PET | 3 | 2 | 1 | 1 |
| C | 1398 | 0.32 | .0075" HDPE and 300d PET | 3 | 1 | 1 | 2 |
| D | 1459 | 0.28 | .0075" HDPE and 450d PET | 3 | 2 | 1 | 3 |
| E | 1398 | 0.32 | .01" HDPE and .0075" HDPE | 3 | 1 | 1 | 3 |
| F | 532 | 0.05 | FEP | 2 | 1 | 1 | 1 |
| G | 3744 | 0.07 | 600d PP and PET | 2 | 1 | 1 | 2 |
| H | 10.5 | 0.45 | 0.219" chenille | 2 | 1 | 1 | 2 |
| I | 10.5 | 0.46 | 0.219" chenille | 2 | 1 | 1 | 3 |
| 5 | 340 | 0.34 | .0075" HDPE 0.016" FEP | 1 | 2 | 1 | 2 |
| 7 | 319 | 0.32 | .0075" HDPE | 1 | 1 | 1 | 3 |
| 8 | 319 | 0.34 | .01" HDPE | 1 | 1 | 1 | 3 | was divided into two halves. Each half of the peeled orange was photographed to illustrate a before image of the orange pith (FIG. 5A). A debridement pad was soaked in sterile water. Excess water was wrung out of the debriding pad. The wet debriding pad was rubbed in a circular pattern on half of the peeled orange for one minute to remove as much orange pith as possible (FIG. 5B). After one minute, the orange was photographed to illustrate an after image of the two halves of the orange (FIG. 5C). A qualitative assessment of the adherence of the orange pith and the ability of the debriding pad to remove the orange pith (pith removal) was recorded. A score of one (1) indicated minimal pith removal, two (2) indicated some pith removal, and three (3) indicated high pith removal. It was noted that adherence of orange pith varied between oranges. For example, some oranges had pith that was easier to remove than other oranges. A qualitative assessment of trauma to the orange was recorded. The trauma assessment represented overly aggressive removal of pith that may be indicative of painful or otherwise overly aggressive debridement of a wound. A score of one (1) indicated no or minimal trauma, two (2) indicated some trauma, and three (3) indicated significant trauma. A qualitative assessment of material shedding or linting was recorded. A score of one (1) indicated no or minimal shedding, two (2) indicated some shedding, and three (3) indicated significant shedding. A qualitative assessment of bottoming out was recorded. Bottoming out included tactic feedback that a support layer or scrim of the debriding pad contacted the pith or surface of the orange. A score of one (1) indicated no or minimal bottoming out, two (2) indicated some bottoming out, and three (3) indicated significant bottoming out. Below is a table summarizing the result of the orange pith test for fourteen debriding pad samples. As indicated in the below table, relatively higher loop height was associated with bottoming out compared to relatively lower loop height. Additionally, or alternative, a combination of loop height of 0.24 mm or less with stiffer and softer Various embodiments of the invention have been described. These and other embodiments are within the scope of the following claims.

The invention claimed is:

1. A debriding pad, comprising:
   a support layer comprising 500 denier multifilament polyester warp yarns, 840 denier multifilament polyester warp yarns, and 2000 denier multifilament polyester weft yarns;
   a first region comprising a first material defining a plurality of first loop piles arranged on the support layer; and
   a second region comprising a second material defining a plurality of second loop piles arranged on the support layer, wherein the second material is stiffer than the first material, and wherein the first region is disposed on a first side of the debriding pad and the second region is disposed on a second side of the debriding pad opposite the first side.

2. The debriding pad of claim 1, wherein the second region further comprises the first material defining a plurality of third loop piles arranged on the support layer.

3. The debriding pad of claim 1, wherein the support layer comprises a scrim, wherein the plurality of first loop piles and the plurality of second loop piles are inserted into the scrim.

4. The debriding pad of claim 1, wherein a linear mass density of the first material is within a range from about 100 denier to about 300 denier.

5. The debriding pad of claim 4, wherein the second material comprises polyester yarn with a linear mass density within a range from about 1200 denier to about 1800 denier.

6. The debriding pad of claim 1, wherein the first material comprises textured polyester yarn.

7. The debriding pad of claim 6, wherein the textured polyester yarn comprises a blend of polyester fibers and natural fibers, the natural fibers comprising at least one of: cotton, or rayon.

8. The debriding pad of claim 1, wherein a linear mass density of the second material is within a range from about 1000 denier to about 2000 denier.

9. The debriding pad of claim 8, wherein the second material comprises monofilament yarn.

10. The debriding pad of claim 1, wherein each loop pile of the plurality of first loop piles comprises about 4 ends of yarn per loop pile.

11. The debriding pad of claim 1, wherein courses per inch of the plurality of second loop piles is within a range from about 15 courses per inch to about 20 courses per inch.

12. The debriding pad of claim 1, wherein an average loop height relative to the support layer of the plurality of first loop piles is within a range from about 5 millimeters (mm) to about 10 mm.

13. The debriding pad of claim 1, wherein an average loop height relative to the support layer of the plurality of second loop piles is within a range from about 5 mm to about 10 mm.

14. The debriding pad of claim 1, wherein a density of the plurality of first loop piles is within a range from about 50 stiches per inch to about 400 stiches per inch.

15. The debriding pad of claim 1, wherein a density of the plurality of second loop piles is within a range from about 50 stiches per inch to about 400 stiches per inch.

16. The debriding pad of claim 1, wherein the debriding pad further comprises at least one of: an absorbent material adjacent to the support layer, or a moisture resistant layer adjacent to the support layer.

17. The debriding pad of claim 1, wherein the debriding pad defines a pocket configured to receive at least a portion of a hand or a distal end of an elongate tool.

18. The debriding pad of claim 1, wherein at least one of the first region or the second region comprises an antimicrobial agent disposed on or within the respective region.

19. A method comprising:

forming, on a support layer, a plurality of first loop piles comprising a first material to define a first region, the support layer comprising 500 denier multifilament polyester warp yarns, 840 denier multifilament polyester warp yarns, and 2000 denier multifilament polyester weft yarns;

forming, on the support layer, a plurality of second loop piles comprising a second material to define a second region, wherein the second material is stiffer than the first material; and securing at least one first free edge of the support layer to at least one second free edge of the support layer to form a debriding pad, wherein the first region is disposed on a first side of the debriding pad and the second region is disposed on a second side of the debriding pad opposite the first side.

20. The method of claim 19, wherein at least one of forming the plurality of first loop piles or forming the plurality of second loop piles comprises knitting at least one of the first material or the second material to the support layer.

* * * * *